(12) United States Patent
Miyamoto

(10) Patent No.: US 11,768,184 B2
(45) Date of Patent: Sep. 26, 2023

(54) METHOD FOR MEASUREMENT OF HEMOGLOBIN

(71) Applicant: ARKRAY, Inc., Kyoto (JP)

(72) Inventor: Mari Miyamoto, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 15 days.

(21) Appl. No.: 17/643,389

(22) Filed: Dec. 8, 2021

(65) Prior Publication Data

US 2022/0187258 A1 Jun. 16, 2022

(30) Foreign Application Priority Data

Dec. 11, 2020 (JP) .................. 2020-205979

(51) Int. Cl.
*G01N 30/86* (2006.01)
*G01N 33/72* (2006.01)
*G01N 30/02* (2006.01)

(52) U.S. Cl.
CPC ....... *G01N 30/8624* (2013.01); *G01N 33/723* (2013.01); *G01N 2030/027* (2013.01)

(58) Field of Classification Search
CPC ............ G01N 30/8624; G01N 33/723; G01N 2030/027; G01N 30/96; G01N 2030/8822; G01N 33/721; G01N 30/06; G01N 30/74; B01D 15/362; B01D 15/12
See application file for complete search history.

(56) References Cited

U.S. PATENT DOCUMENTS

2021/0278422 A1* 9/2021 Oishi .................... G01N 30/06

FOREIGN PATENT DOCUMENTS

| JP | 2003-344372 A | 12/2003 | | |
|---|---|---|---|---|
| JP | 2006-081471 A | 3/2006 | | |
| JP | 2007-163182 A | 6/2007 | | |
| JP | 2007163182 A | * | 6/2007 | |
| JP | 2010107436 A | * | 5/2010 | |
| JP | 6651066 B1 | 2/2020 | | |
| WO | WO-2020054572 A1 | * | 3/2020 | ........... B01D 15/362 |

OTHER PUBLICATIONS

The extended European search report issued by the European Patent Office dated May 11, 2022, which corresponds to European Patent Application No. 21213819.2-1101 and is related to U.S. Appl. No. 17/643,389.
Communication pursuant to Article 94(3) EPC issued by the European Patent Office dated Jan. 19, 2023, which corresponds to European Patent Application No. 21213819.2-1101 and is related to U.S. Appl. No. 17/643,389.

* cited by examiner

*Primary Examiner* — Jill A Warden
*Assistant Examiner* — Michael Paul Shimek
(74) *Attorney, Agent, or Firm* — Studebaker & Brackett PC

(57) ABSTRACT

A reagent for use in the measurement of hemoglobins by liquid chromatography, the reagent comprising a nonionic surfactant selected from the group consisting of:

(i) polyoxyethylene (10) decyl ether; (ii) polyoxyethylene (6) 2-ethylhexyl ether; (iii) polyoxyethylene (9) isodecyl ether; (iv) polyoxyethylene (10) nonyl ether; (v) polyoxyethylene (16) isostearyl ether; (vi) polyoxyethylene (20) behenyl ether; and (vii) polyoxyethylene (20) polyoxypropylene (6) decyltetradecyl ether.

8 Claims, 3 Drawing Sheets

METHOD FOR MEASUREMENT OF HEMOGLOBIN

TECHNICAL FIELD

The present invention relates to a reagent for the measurement of hemoglobins by liquid chromatography, and a method of measuring hemoglobins using the reagent.

BACKGROUND ART

By entrance of blood sugar into erythrocytes followed by chemical bonding of the sugar to hemoglobin (hereinafter simply referred to as Hb), hemoglobin A1c (hereinafter simply referred to as HbA1c) is produced. HbA1c reflects the average blood glucose level (glucose concentration in blood) during the past one to two months. Therefore, HbA1c is widely used as an index in screening tests for diabetes, and as an index for diagnosis of diabetes, for example, for determining the state of blood glucose control in patients with diabetes.

For measurement of hemoglobins including HbA1c, high-performance liquid chromatography is widely used. In this measurement, Triton X-100 (registered trademark) has been conventionally used as a surfactant having a hemolytic effect for preparation of a measurement sample from blood.

However, in recent years, use of surfactants that adversely affect the environment has been regulated by the REACH regulation in Europe, and Triton X-100 has become a compound that is regulated by the REACH regulation. In view of this, Patent Document 1 discloses hemolysis reagents for measurement of hemoglobins by liquid chromatography, the reagents comprising a surfactant other than Triton X-100. However, since only a limited number of hemolysis reagents have been disclosed in Patent Document 1, reagents which enable highly accurate measurement of hemoglobins by liquid chromatography without largely affecting the environment have further been demanded.

PRIOR ART DOCUMENT

Patent Document

[Patent Document 1] JP 6651066 B

SUMMARY OF THE INVENTION

One aspect of the present invention is to provide a measurement reagent for obtaining highly accurate measurement results in the measurement of hemoglobins by liquid chromatography.

In order to solve the above problem, the present inventors intensively studied. As a result, the present inventors discovered that, by carrying out liquid chromatography using a nonionic surfactant selected from the group consisting of the following (i) to (vii), highly accurate and highly reproducible measurement of hemoglobins is possible, thereby completed the present invention.

More specifically, in one aspect of the present invention, there is provided a reagent for measurement of hemoglobin by liquid chromatography,
the reagent comprising a nonionic surfactant selected from the group consisting of the following (i) to (vii):
(i) polyoxyethylene (10) decyl ether;
(ii) polyoxyethylene (6) 2-ethylhexyl ether;
(iii) polyoxyethylene (9) isodecyl ether;
(iv) polyoxyethylene (10) nonyl ether;
(v) polyoxyethylene (16) isostearyl ether;
(vi) polyoxyethylene (20) behenyl ether; and
(vii) polyoxyethylene (20) polyoxypropylene (6) decyltetradecyl ether.

In another aspect of the present invention, there is provided a method of measuring hemoglobins by liquid chromatography, using the reagent comprising a nonionic surfactant selected from the group consisting of the above (i) to (vii).

In another aspect of the present invention, there is provided a use of a reagent comprising a nonionic surfactant in measuring hemoglobins by liquid chromatography, wherein said nonionic surfactant is one or more nonionic surfactants selected from the group consisting of the above (i) to (vii).

Advantageous Effects of the Invention

According to the present invention, a good measurement result can be obtained in the measurement of hemoglobins by liquid chromatography. By using the nonionic surfactant described above, erythrocytes contained in an erythrocyte-containing sample (specimen) such as blood can be efficiently lysed, so that a measurement sample can be efficiently prepared. Furthermore, since excellent peak resolution can be achieved in liquid chromatography, highly accurate measurement of hemoglobins is possible. Furthermore, even in cases where a long time has passed after preparation of a mixture of a specimen and a hemolysis reagent, highly reproducible and accurate hemoglobin measurement values can be obtained in the measurement of hemoglobins in the mixture.

Figure 1:
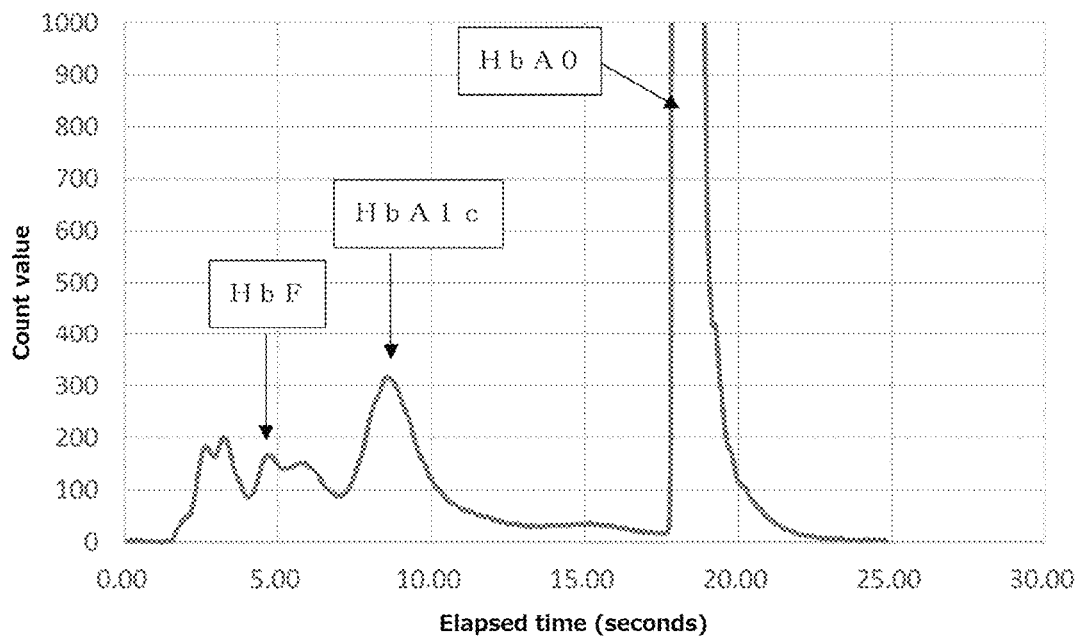
FIG. 1 shows a diagram illustrating an example of a good chromatogram in a case where hemoglobins were measured in the first mode.

EMBODIMENTS FOR CARRYING OUT THE INVENTION (Reagent for Measurement of Hemoglobins)

The reagent for use in the measurement of hemoglobins comprises one or more nonionic surfactants selected from the group consisting of:
(i) polyoxyethylene (10) decyl ether;
(ii) polyoxyethylene (6) 2-ethylhexyl ether;
(iii) polyoxyethylene (9) isodecyl ether;
(iv) polyoxyethylene (10) nonyl ether;
(v) polyoxyethylene (16) isostearyl ether;
(vi) polyoxyethylene (20) behenyl ether; and
(vii) polyoxyethylene (20) polyoxypropylene (6) decyltetradecyl ether.

Here, each numeral in parentheses represents the number, in moles, of oxyethylene groups or polyoxypropylene groups added, and the number in moles can be calculated from the molecular weight of each polyoxyethylene alkyl ether.

Of (i) to (vii), it is more preferred to use the nonionic surfactant of any of (i) (iii), and (v).

Although the structure of each nonionic surfactant can be unambiguously specified based on the compound name, the structures of (iii), (v), and (vii) are shown below for further clarification.

(iii) Polyoxyethylene (9) isodecyl ether

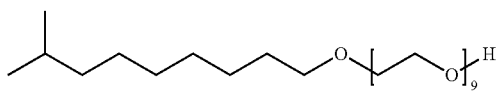

(v) Polyoxyethylene (16) isostearyl ether

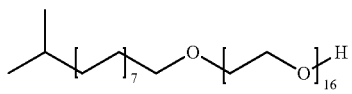

(vii) Polyoxyethylene (20) polyoxypropylene (6) decyltetradecyl ether

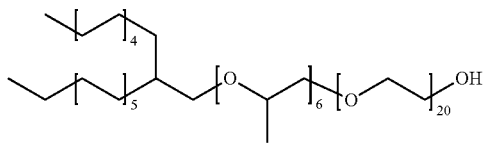

The reagent to be used for the measurement of hemoglobins is preferably a liquid reagent, preferably an aqueous solution. The content of the nonionic surfactant in the reagent is preferably 0.01% by weight to 1.0% by weight, more preferably 0.05% by weight to 1.0% by weight, still more preferably 0.05% by weight to 0.75% by weight, especially preferably 0.09% by weight to 0.50% by weight.

The surfactant may be dissolved before use to a preferred concentration in a solvent such as water to prepare the reagent.

The reagent to be used for measurement of hemoglobins may contain two or more kinds of surfactants described above.

When the reagent to be used for measurement of hemoglobins contains two or more kinds of surfactants described above, the total content of the surfactants is preferably within the range described above.

The reagent to be used for measurement of hemoglobins preferably contains a buffer substance. By the inclusion of the buffer substance, the pH can be maintained within a certain range, for example, within the range of 6.0 to 8.5, preferably 6.5 to 8.0, more preferably 6.8 to 7.5.

Examples of the buffer substance include phosphoric acid salts such as sodium phosphate, disodium hydrogen phosphate, sodium dihydrogen phosphate, potassium phosphate, dipotassium hydrogen phosphate, and potassium dihydrogen phosphate; carbonic acid salts such as sodium carbonate and sodium hydrogen carbonate; boric acid salts such as sodium borate; carboxylic acid; dicarboxylic acid; carboxylic acid derivatives; hydroxycarboxylic acid; aniline; aniline derivatives; amino acid; amine compounds; imidazole compounds; alcohol compounds; ethylenediaminetetraacetic acid; pyrophosphate; pyridine; cacodylic acid; glycerol phosphate; 2,4,6-collidine; N-ethylmorpholine; morpholine; 4-aminopyridine; ammonia; ephedrine; hydroxyproline; piperidine; tris(hydroxymethyl)aminomethane; and glycylglycine. The concentration of the buffer substance contained in the reagent for measurement of hemoglobins is not limited as long as a buffering action can be produced. The concentration of the buffer substance contained in the reagent for measurement of hemoglobins may be 0.5 mM to 50 mM, preferably 1 mM to 10 mM.

The reagent to be used for measurement of hemoglobins preferably contains an inorganic salt. By the inclusion of the inorganic salt, the osmotic pressure can be adjusted within a certain range.

Examples of the inorganic salt include sodium chloride, potassium chloride, sodium sulfate, and potassium sulfate.

The reagent to be used for measurement of hemoglobins may also contain a component such as an antiseptic or a hemoglobin stabilizer.

Examples of the antiseptic include methylparaben, phenoxyethanol, sodium azide, thymol, and sodium propionate.

Examples of the hemoglobin stabilizer include chelating agents such as ethylenediaminetetraacetic acid (EDTA); and glutathione. The concentrations of the hemoglobin stabilizer and the antiseptic contained in the reagent for measurement of hemoglobins are not limited. They may each be contained at a concentration of 0.01% by weight to 0.3% by weight, preferably 0.02% by weight to 0.2% by weight.

Hemoglobins are measured by liquid chromatography.

Here, the liquid chromatography is preferably high-performance liquid chromatography (HPLC), and the separation method is preferably cation-exchange chromatography.

The cation-exchange column used in the cation-exchange liquid chromatography is not limited as long as hemoglobin can be adsorbed thereto, and known cation-exchange columns may be used. For example, a column packed with a filler containing a cation-exchange group such as a carboxyl group, sulfonate group, or phosphate group may be used. Specific examples of the column include, but are not limited to, "Column Unit 90" for use in a glycohemoglobin analyzer ADAMS A1c HA-8190V, manufactured by Arkray, Inc.

Examples of the hemoglobins (Hb) to be measured include, but are not limited to, HbA1c, HbF, HbS, HbC, HbE, and HbD. Of these, HbA1c and HbF are preferred, and HbA1c is more preferred. Two or more kinds of hemoglobins may be measured.

The reagent is used for measuring hemoglobins by liquid chromatography.

The reagent to be used for measurement of hemoglobins may be used as a washing liquid, an eluent, or a diluent for standard samples, in liquid chromatography. However, the reagent is preferably used to prepare a measurement sample for liquid chromatography. A measurement sample can be prepared by treating a hemoglobin-containing sample with the reagent comprising the above nonionic surfactant. The hemoglobin-containing sample is not limited as long as it contains hemoglobin but is preferably an erythrocyte-containing sample, and especially a blood sample.

The reagent comprising the above nonionic surfactant can preferably be used to release hemoglobin from the hemoglobin-containing sample and more specifically, can be used as a hemolysis reagent for hemolysis of erythrocytes contained in an erythrocyte-containing sample, especially a blood sample.

In cases where the reagent comprising the above nonionic surfactant is added to an erythrocyte-containing sample to cause hemolysis of erythrocytes for preparation of a measurement sample, the reagent for measurement of hemoglobins may be added in an amount sufficient to effect hemolysis of the erythrocytes. For example, the volume of the reagent to be added to the erythrocyte-containing sample is preferably not less than 10 times, not less than 50 times, or not less than 100 times the volume of the sample, and preferably not more than 500 times, or not more than 250 times the volume of the sample.

(Method of Measuring Hemoglobins)

The method of measuring hemoglobins according to an aspect of the present invention comprises: treating a hemoglobin-containing sample such as an erythrocyte-containing sample with the above-described reagent comprising the above nonionic surfactant to obtain a mixture (measurement sample); and subjecting the mixture to measurement by liquid chromatography.

A description is given below by way of an example of cation-exchange liquid chromatography as a preferred mode.

The cation-exchange liquid chromatography may be carried out according to a known procedure.

Specific examples of the method include a method in which the reagent comprising the above nonionic surfactant is added to, and mixed with, a hemoglobin-containing sample such as an erythrocyte-containing sample including a blood sample, to prepare a measurement sample, and the measurement sample is loaded onto a column to allow adsorption of hemoglobins to the column, followed by washing the column, eluting the hemoglobins, and then detecting the hemoglobins by measurement of the absorbance or the like.

The elution may be carried out using an eluent having a different salt concentration or an eluent having a different pH, to allow elution of components adsorbed to the column while changing the salt concentration or the pH. Examples of the salt include, but are not limited to, sodium chloride.

When the salt concentration or the pH is changed, it may be changed continuously (linear gradient method), or may be changed stepwise (step gradient method).

Alternatively, for example, HbF and/or HbA1c may be analyzed by a first mode, wherein a first eluent is applied to a column containing hemoglobins adsorbed thereto, to elute HbF and/or HbA1c, and then a second eluent (washing liquid) having a stronger elution strength for eluting hemoglobins adsorbed to the column than the first eluent is applied to elute the remaining hemoglobins adsorbed to the column.

Alternatively, hemoglobins (such as HbS, HbC, HbE, and/or HbD) having a higher adsorbability to the column than HbF and/or HbA1c may be analyzed in detail by a second mode, wherein a first eluent is applied to a column containing hemoglobins adsorbed thereto, to elute HbF and/or HbA1c, and then a third eluent having a higher elution strength than the first eluent but having a lower elution strength than the second eluent is applied.

Based on a chromatogram obtained by absorbance measurement or the like, the presence, the shape, the intensity, and/or the area of a target peak corresponding to each hemoglobin may be measured to detect and quantify the hemoglobin. For example, the ratio of the peak area of hemoglobin A1c to the total peak area of hemoglobin may be used as a measured value of hemoglobin A1c (HbA1c %). Similarly, the ratio of the peak area of hemoglobin F to the total peak area of hemoglobin may be used as a measured value of hemoglobin F (HbF %).

A calibration curve(s) may be prepared by performing measurement using a standard sample(s) with known concentrations of hemoglobins, and the concentrations of the hemoglobins in a specimen may be calculated based on the calibration curve(s).

Examples

Hereinafter, the present invention is described below concretely with reference to Examples. However, the present invention is not limited to the following embodiments.

1. Preparation of Reagents for Measurement of Hemoglobins

As shown in Table 1, dipotassium hydrogen phosphate, EDTA-2Na, a nonionic surfactant, and water were mixed together to prepare the reagents of Example 1 to Example 14 for measurement of hemoglobins.

The nonionic surfactants used for the reagents for measurement of hemoglobins are shown in Table 2. The concentrations of dipotassium hydrogen phosphate and EDTA-2Na contained in the reagents for measurement of hemoglobins are 5.2 mM and 1.3 mM, respectively.

TABLE 1

| | Content (% by weight) in the reagent for measurement of hemoglobins |
|---|---|
| Dipotassium hydrogen phosphate | 0.090% |
| EDTA-2Na | 0.050% |
| Nonionic surfactant | 0.09% or 0.5% |
| Water | Remainder |

TABLE 2

| | Product name of nonionic surfactant | Chemical name or common name | Content |
|---|---|---|---|
| Reference Example | Triton X-100 | Polyoxyethylene (9.5) glycol mono-p-isooctylphenyl ether | 0.09% |
| Example 1 | FINESURF D-1310 | Polyoxyethylene (10) decyl ether | 0.09% |
| Example 2 | FINESURF D-1310 | Polyoxyethylene (10) decyl ether | 0.50% |
| Example 3 | BLAUNON EH-6 | Polyoxyethylene (6) 2-ethylhexyl ether | 0.09% |
| Example 4 | BLAUNON EH-6 | Polyoxyethylene (6) 2-ethylhexyl ether | 0.50% |
| Example 5 | SAFETYCUT ID-1087 | Polyoxyethylene (9) isodecyl ether | 0.09% |
| Example 6 | SAFETYCUT ID-1087 | Polyoxyethylene (9) isodecyl ether | 0.50% |
| Example 7 | BLAUNON OX-910 | Polyoxyethylene (10) nonyl ether | 0.09% |
| Example 8 | BLAUNON OX-910 | Polyoxyethylene (10) nonyl ether | 0.50% |
| Example 9 | FINESURF FO-160 | Polyoxyethylene (16) isostearyl ether | 0.09% |
| Example 10 | FINESURF FO-160 | Polyoxyethylene (16) isostearyl ether | 0.50% |
| Example 11 | BLAUNON BE-20 | Polyoxyethylene (20) behenyl ether | 0.09% |
| Example 12 | BLAUNON BE-20 | Polyoxyethylene (20) behenyl ether | 0.50% |

TABLE 2-continued

| | Product name of nonionic surfactant | Chemical name or common name | Content |
|---|---|---|---|
| Example 13 | BLAUNON DC-620 | Polyoxyethylene (20) polyoxypropylene (6) decyltetradecyl ether | 0.09% |
| Example 14 | BLAUNON DC-620 | Polyoxyethylene (20) polyoxypropylene (6) decyltetradecyl ether | 0.50% |

Triton X-100 was obtained from Nacalai Tesque, Inc., and the others were obtained from Aoki Oil Industrial Co., Ltd.

2. Evaluation of Reagents for Measurement of Hemoglobins 2-1-1. Evaluation of Hemolytic Capacity In a 1.5-mL Eppendorf tube, 1 mL of each reagent for measurement of hemoglobins prepared in 1 above, and 10 µL of whole blood containing erythrocytes were placed, to prepare a mixture of the reagent for measurement of hemoglobins and the whole blood. The Eppendorf tube was centrifuged, and the color of the supernatant of the mixture and the presence or absence of a pellet generated in the bottom of the Eppendorf tube were visually observed.

The hemolytic capacity was judged according to the following standard.

TABLE 3

| Rating of hemolytic capacity | Supernatant color | Presence or absence of a pellet |
|---|---|---|
| Excellent (⊚) | Reddish | Absent |
| Good (○) | Reddish | Present |
| Poor (×) | Non-reddish | Present |

2-1-2. Evaluation of Stability after Mixing

In a 7-mL PP vial container, 3 mL of each reagent for measurement of hemoglobins prepared in 1 above and 30 µL of a whole blood specimen were mixed to prepare a mixture.

HbA1c and HbF contained in the prepared mixture were measured by liquid chromatography on the day when the mixture was prepared.

After the measurement, the mixture solution was stored at room temperature. On the next day, HbA1c and HbF contained in the mixture were similarly measured.

The difference (ΔHbA1c) between the measured value of HbA1c (HbA1c %) obtained by the measurement on the day when the mixture was prepared and the measured value of HbA1c (HbA1c %) obtained by the measurement on the next day was determined.

Similarly, the difference (ΔHbF) between the measured value of HbF (HbF %) obtained by the measurement on the day when the mixture was prepared and the measured value of HbF (HbF %) obtained by the measurement on the next day was determined.

The measurement was carried out under the following conditions.

Measurement Conditions for Liquid Chromatography
 Measurement apparatus: glycohemoglobin analyzer ("HA-8190V", manufactured by Arkray, Inc.)
 Measurement principle: reversed-phase partition cation-exchange chromatography
 Measurement wavelength: 420.5 nm/500 nm
 Eluents:
  First eluent
  Second eluent
  Third eluent The hemoglobin elution strength is highest in the second eluent, followed by the third eluent and the first eluent in that order.

Measurement Conditions:

Hemoglobins were measured by the first mode, wherein the first eluent described above was applied to the column to allow elution of HbF and HbA1c, and then the second eluent was applied to the column to allow elution of all hemoglobin remaining on the column.

In addition, hemoglobins were measured by the second mode, wherein the first eluent was applied to the column to allow elution of HbF and HbA1c, and then the third eluent was applied to the column to allow elution of HbS, HbC, HbE, and HbD, followed by applying the second eluent to the column to allow elution of all hemoglobin remaining on the column.

The stability after mixing was evaluated according to the following standard.

TABLE 4

| Rating of stability after mixing | HbA1c % | HbF % |
|---|---|---|
| Good (○) | ΔHbA1c was not more than 0.1%. | ΔHbF was not more than 0.1%. |
| Poor (×) | ΔHbA1c was more than 0.1%. | ΔHbF was more than 0.1%. |

2-1-3. Evaluation of Resolution

In a 7-mL PP vial container, 3 mL of each reagent for measurement of hemoglobins prepared in 1 above and 30 µL of an actual specimen were mixed to prepare a mixture.

The prepared mixture was subjected to measurement by liquid chromatography in the same manner as in 2-1-2 above, to obtain a chromatogram.

Thereafter, the mixture solution was stored at room temperature, and, on the next day, the mixture was subjected to measurement by liquid chromatography in the same manner as in the above 2-1-2, to obtain a chromatogram.

From the chromatogram obtained on the day when the mixture was prepared, the time (Td1) between the beginning of separation of hemoglobins and the detection of the HbA1c peak, and the width (T0.5w1) between the points exhibiting the half value of the peak height in the HbA1c peak were determined, and the resolution (R1) was determined according to the Equation (I) shown below.

Similarly, from the chromatogram obtained on the next day of the preparation of the mixture, the time (Td2) between the beginning of separation of hemoglobins and the detection of the HbA1c peak, and the width (T0.5w2) between the points exhibiting the half value of the peak height in the HbA1c peak were determined, and the resolution (R2) was determined according to the Equation (I).

It should be noted that the value of the resolution increases as Td increases, and as T0.5W decreases. As the value of the resolution increases, the capacity to separate HbA1c from other hemoglobins increases.

$$R = Td/T0.5W \qquad (I)$$

R: Resolution
Td: Time between the beginning of separation of hemoglobins and the detection of the HbA1c peak
T0.5W: Width between the points exhibiting the half value of the peak height in the HbA1c peak (half-width)

The resolution was evaluated according to the following standard.

TABLE 5

| Rating of resolution | Resolution |
|---|---|
| Good (○) | \|R1 − R2\| ≤ 0.25 |
| Poor (×) | \|R1 − R2\| > 0.25 |

2-2. Results of Evaluation of Hemolytic Capacity, Stability after Mixing, and Resolution Table 6 shows the results of evaluation of the hemolytic capacity, the stability after mixing, and the resolution.

All of Example 1 to Example 14 exhibited good hemolytic capacities.

Further, Example 1 to Example 14 exhibited good stability after mixing in terms of both the measured value of HbA1c and the measured value of HbF.

This is considered to be due to the fact that the nonionic surfactants contained in Example 1 to Example 14 have only low levels of actions causing denaturation of hemoglobins.

The above results indicate that the reagents of Example 1 to Example 14 for measurement of hemoglobins are useful for measuring hemoglobins by liquid chromatography.

Examples 1, 2, 4, 5, 6, 8, 9, 10, and 12 are preferred because of their excellent hemolytic capacities.

TABLE 6

| | Hemolytic capacity | Stability after mixing (HbA1c %) | | Stability after mixing (HbF %) | | Resolution | |
|---|---|---|---|---|---|---|---|
| | | First mode | Second mode | First mode | Second mode | First mode | Second mode |
| Reference Example | ◉ | ○ | ○ | ○ | ○ | ○ | ○ |
| Example 1 | ◉ | ○ | ○ | ○ | ○ | ○ | ○ |
| Example 2 | ◉ | ○ | ○ | ○ | ○ | ○ | ○ |
| Example 3 | ○ | ○ | ○ | ○ | ○ | ○ | ○ |
| Example 4 | ◉ | ○ | ○ | ○ | ○ | ○ | ○ |
| Example 5 | ◉ | ○ | ○ | ○ | ○ | ○ | ○ |
| Example 6 | ◉ | ○ | ○ | ○ | ○ | ○ | ○ |
| Example 7 | ○ | ○ | ○ | ○ | ○ | ○ | ○ |
| Example 8 | ◉ | ○ | ○ | ○ | ○ | ○ | ○ |
| Example 9 | ◉ | ○ | ○ | ○ | ○ | ○ | ○ |
| Example 10 | ◉ | ○ | ○ | ○ | ○ | ○ | ○ |
| Example 11 | ○ | ○ | ○ | ○ | ○ | ○ | ○ |
| Example 12 | ◉ | ○ | ○ | ○ | ○ | ○ | ○ |
| Example 13 | ○ | ○ | ○ | ○ | ○ | ○ | ○ |
| Example 14 | ○ | ○ | ○ | ○ | ○ | ○ | ○ |

2-3. Evaluation of Chromatogram Shape
2-3-1. Evaluation of Chromatogram Shape

Mixtures were prepared in the same manner as described above, and stored at room temperature.

On the next day, each mixture that had been stored was subjected to measurement in the same manner as in 2-1-2 above, to obtain a chromatogram.

FIG. 1 to FIG. 5 show examples of chromatograms. In each of FIG. 1 to FIG. 5, the abscissa represents the elapsed time (seconds) after the beginning of the separation (beginning of the measurement), and the ordinate represents the count value in accordance with the absorbance (420.5 nm) of hemoglobin. In each of FIG. 1 to FIG. 5, the peaks of HbF, HbA1c, and HbA0 are shown. In the chromatogram of each of FIG. 1 to FIG. 5, the peak that appears at an elapsed time of about 4.8 seconds is the peak of HbF; the peak that appears at an elapsed time of about 8.5 seconds is the peak of HbA1c; and the peak that appears at an elapsed time of about 18 seconds to about 21 seconds is the peak of HbA0.

In some Examples, peaks may be detected as noises in regions where no peaks are originally detected. These noise peaks appear at various times depending on the conditions for the hemoglobin measurement, such as the cation-exchange column used for the hemoglobin measurement, the type of the eluent, and the conditions of application of the eluent. Under this measurement condition, noise peaks appeared at about 1.7 seconds and about 22 seconds in the first mode, and at about 1.7 seconds and about 52.4 seconds in the second mode.

FIG. 1 shows a good chromatogram in a case where the hemoglobins were measured in the first mode.

Figure 2:
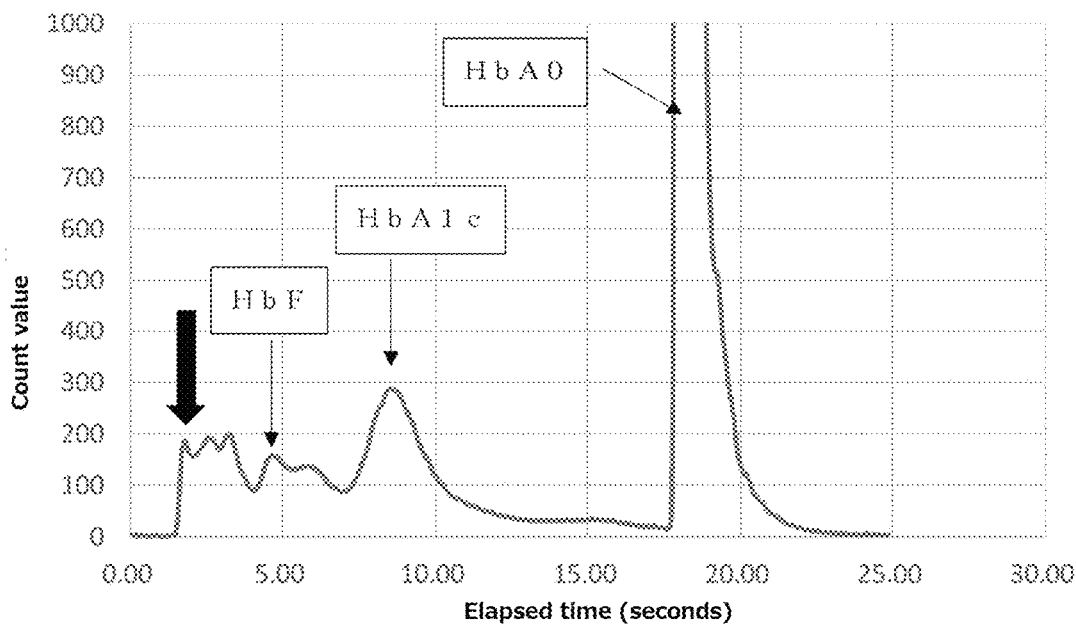
FIG. 2 shows a diagram illustrating an example of a chromatogram having a noise peak in a case where hemoglobins were measured in the first mode (Part 1). The arrowhead indicates the noise peak.

As in the chromatogram shown in FIG. 2, in cases where hemoglobins are measured in the first mode, some Examples may exhibit a noise peak detected at about 1.7 seconds after the beginning of the measurement.

Figure 3:
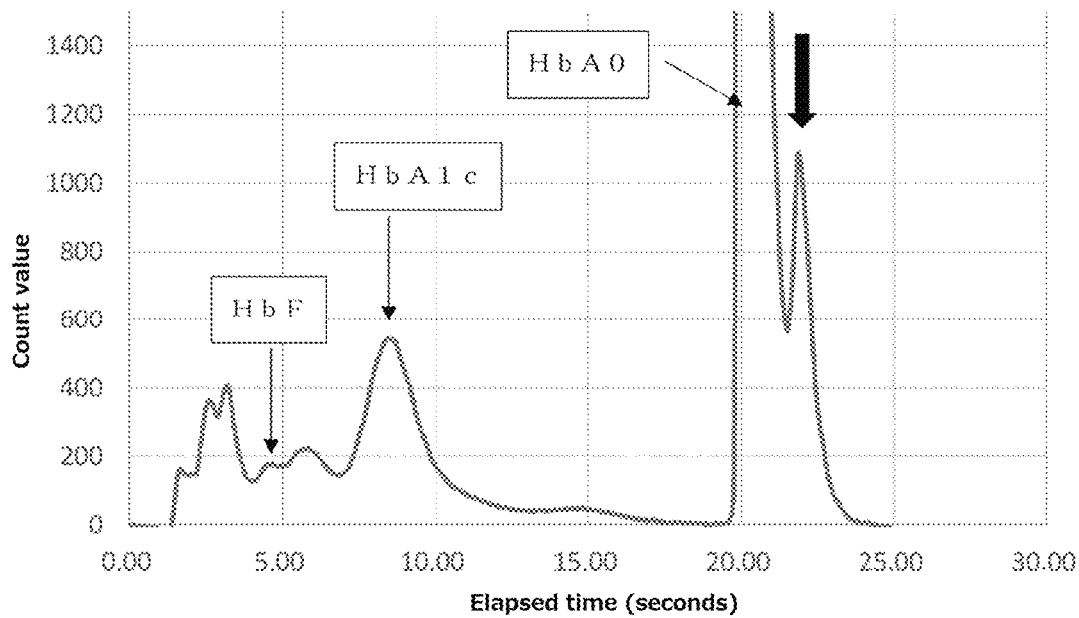
FIG. 3 shows a diagram illustrating an example of a chromatogram having a noise peak in a case where hemoglobins were measured in the first mode (Part 2). The arrowhead indicates the noise peak.

As shown in FIG. 3, some Examples may exhibit a noise peak detected at about 22 seconds, which follows the HbA0 peak.

Figure 4:
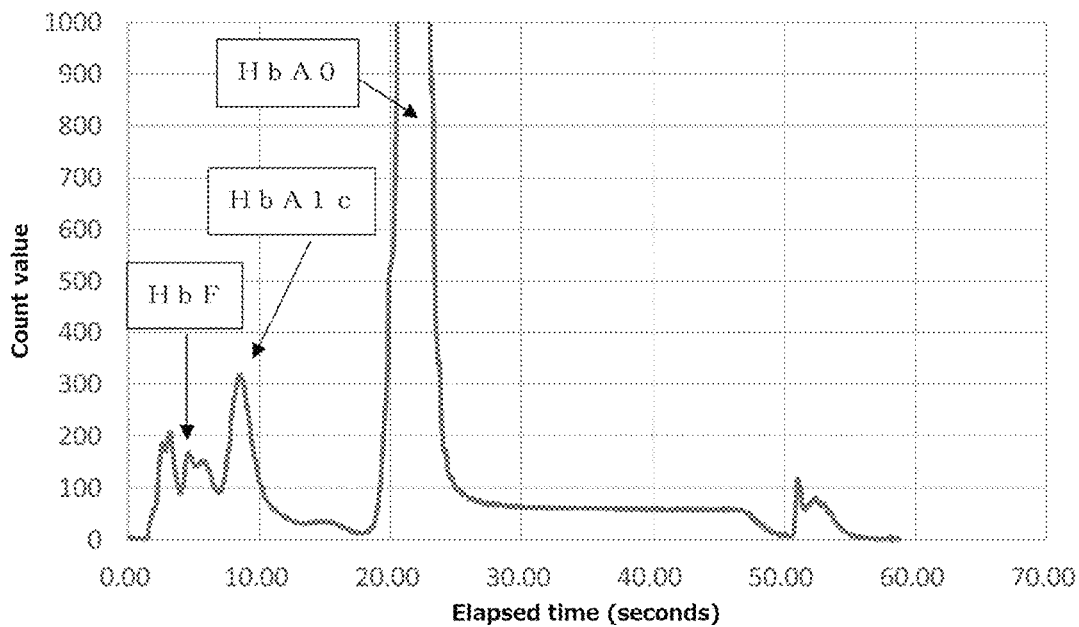
FIG. 4 shows an example of a good chromatogram in a case where hemoglobins were measured in the second mode.

FIG. 4 shows a good chromatogram in a case where the hemoglobins were measured in the second mode.

Figure 5:
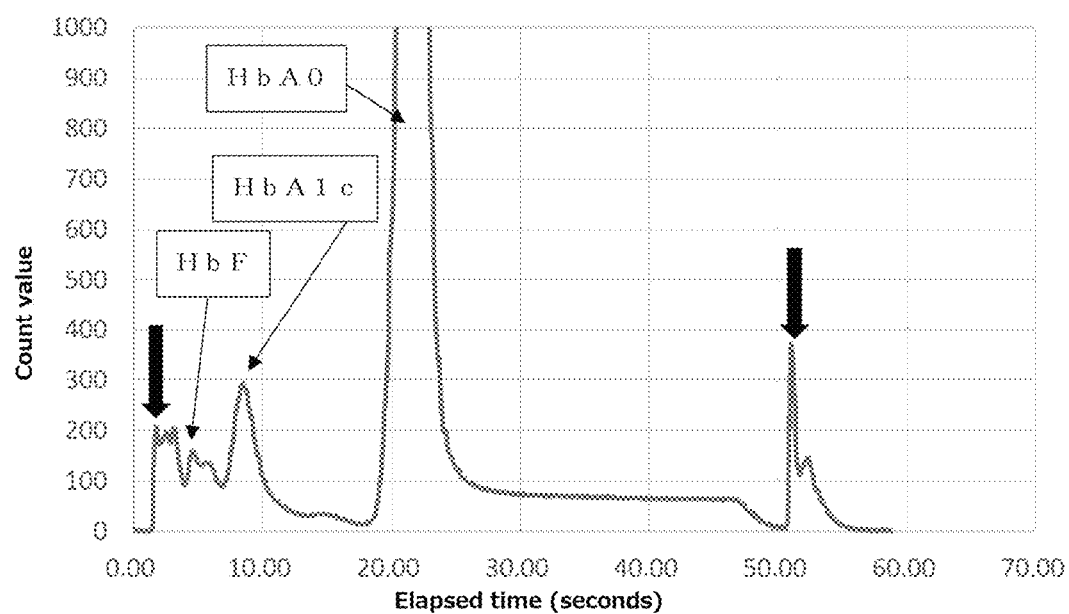
FIG. 5 shows an example of a chromatogram having noise peaks in a case where hemoglobins were measured in the second mode. The arrowheads indicate the noise peaks.

As in the chromatogram shown in FIG. 5, in cases where hemoglobins are measured in the second mode, some Examples may exhibit noise peaks detected at about 1.7 seconds and about 52.4 seconds after the beginning of the measurement.

In the measurement conditions, the noise peaks do not affect the measurement of HbA1c, HbF, and variant Hb. However, unnecessary noise peaks are preferably absent in the chromatogram.

The chromatogram shape was evaluated according to the following standard.

TABLE 7

| Rating of chromatogram shape | Peak (First mode) | | Peak (Second mode) | |
|---|---|---|---|---|
| | At about 1.7 seconds | At about 22 seconds | At about 1.7 seconds | At about 52.4 seconds |
| Good (○) | Lower peak value than the peak value in Reference Example | | | |
| Fair (Δ) | Higher peak value than the peak value in Reference Example | | | |

Overall evaluation of the peak shape was carried out as follows.

TABLE 8

| | Peak Shape (First mode) | | Peak Shape (Second mode) | |
|---|---|---|---|---|
| Overall Evaluation | At about 1.7 seconds | At about 22 seconds | At about 1.7 seconds | At about 52.4 seconds |
| Very Good (◎) | ○ | ○ | ○ | ○ |
| Good (○) | Rated as ○ in at least one of the evaluations. | | | |
| Fair (Δ) | Rated as ○ in none of the evaluations. | | | |

2-3-2. Evaluation Results of Chromatogram Shape

Table 9 shows the results of evaluation of the chromatogram shape.

From the evaluation results, it was found that Examples 1, 3, 4, 5, 7, and 9 to 14 are good reagents for measurement of hemoglobins.

In particular, Examples 1, 5, and 9 were found to be excellent reagents for measurement of hemoglobins.

TABLE 9

| | Peak Shape (First mode) | | Peak Shape (Second mode) | | |
|---|---|---|---|---|---|
| | At about 1.7 seconds | At about 22 seconds | At about 1.7 seconds | At about 52.4 seconds | Overall evaluation |
| Reference Example | ○ | ○ | ○ | ○ | ◎ |
| Example 1 | ○ | ○ | ○ | ○ | ◎ |
| Example 2 | Δ | — | Δ | Δ | Δ |
| Example 3 | ○ | Δ | ○ | ○ | ○ |
| Example 4 | Δ | — | Δ | ○ | ○ |
| Example 5 | ○ | ○ | ○ | ○ | ◎ |
| Example 6 | Δ | — | Δ | Δ | Δ |
| Example 7 | ○ | Δ | ○ | ○ | ○ |
| Example 8 | Δ | — | Δ | Δ | Δ |
| Example 9 | ○ | ○ | ○ | ○ | ◎ |
| Example 10 | ○ | — | ○ | Δ | ○ |
| Example 11 | ○ | Δ | ○ | Δ | ○ |
| Example 12 | ○ | — | ○ | ○ | ○ |
| Example 13 | ○ | ○ | ○ | ○ | ○ |
| Example 14 | ○ | — | ○ | Δ | ○ |

While the invention has been described in detail with reference to exemplary embodiments thereof, it will be apparent to one skilled in the art that various changes may be made, and equivalents employed, without departing from the scope of the invention. Each of the aforementioned documents as well as JP2020-205979 is incorporated by reference herein in its entirety.

The invention claimed is:

1. A method of measuring one or more hemoglobins by liquid chromatography, comprising:
    treating a hemoglobin-containing sample with a reagent comprising a nonionic surfactant,
    performing liquid chromatography using the hemoglobin-containing sample treated with the reagent, and
    detecting and measuring at least one peak of the one or more hemoglobins in a liquid chromatogram to quantify the one or more hemoglobins,
    wherein said nonionic surfactant is one or more nonionic surfactants selected from the group consisting of:
    (i) polyoxyethylene (10) decyl ether;
    (ii) polyoxyethylene (6) 2-ethylhexyl ether;
    (iii) polyoxyethylene (9) isodecyl ether;
    (iv) polyoxyethylene (10) nonyl ether;
    (v) polyoxyethylene (20) behenyl ether; and
    (vi) polyoxyethylene (20) polyoxypropylene (6) decyltetradecyl ether.

2. The method according to claim 1, wherein the nonionic surfactant is one or more nonionic surfactants selected from the group consisting of:
    (i) polyoxyethylene (10) decyl ether; and
    (iii) polyoxyethylene (9) isodecyl ether.

3. The method according to claim 1, wherein said reagent contains 0.01% by weight to 1.0% by weight of the nonionic surfactant.

4. The method according to claim 1, wherein said hemoglobin-containing sample is an erythrocyte-containing sample.

5. The method according to claim 4, wherein said erythrocyte-containing sample is a blood sample.

6. The method according to claim 1, wherein the liquid chromatography is cation-exchange liquid chromatography.

7. The method according to claim 1, wherein the reagent comprises only one nonionic surfactant.

8. The method according to claim 1, wherein the nonionic surfactant is one selected from the group consisting of:
    (v) polyoxyethylene (20) behenyl ether; and
    (vi) polyoxyethylene (20) polyoxypropylene (6) decyltetradecyl ether.

* * * * *